(12) United States Patent  
Gupta et al.

(10) Patent No.: US 8,524,893 B2  
(45) Date of Patent: Sep. 3, 2013

(54) PROCESS FOR THE PREPARATION OF TEMSIROLIMUS AND ITS INTERMEDIATES

(75) Inventors: Nitin Gupta, Ghaziabad (IN); Vishal Handa, Ghaziabad (IN); Abir Kumar Pal, Ghaziabed (IN); Hemant Kumar Singh, Ghaziabad (IN); Saswata Lahiri, Ghaziabad (IN); Sushil Kumar Dubey, Ghaziabad (IN)

(73) Assignee: Fresenius Kabi Oncology Limited, New Delhi (IN)

( * ) Notice: Subject to any disclaimer, the term of this patent is extended or adjusted under 35 U.S.C. 154(b) by 301 days.

(21) Appl. No.: 13/016,235

(22) Filed: Jan. 28, 2011

(65) Prior Publication Data

US 2011/0184167 A1   Jul. 28, 2011

(30) Foreign Application Priority Data

Jan. 28, 2010   (IN) .............................. 173/DEL/2010

(51) Int. Cl.
 *C07D 498/00*   (2006.01)
(52) U.S. Cl.
 USPC ........................................................ 540/456
(58) Field of Classification Search
 None
 See application file for complete search history.

(56) References Cited

U.S. PATENT DOCUMENTS

| | | | |
|---|---|---|---|
| 5,362,718 A | 11/1994 | Skotnicki et al. | |
| 6,277,983 B1 | 8/2001 | Shaw et al. | |
| 7,153,957 B2 | 12/2006 | Chew et al. | |
| 2010/0249415 A1 | 9/2010 | Lee et al. | |

*Primary Examiner* — Noble Jarrell  
(74) *Attorney, Agent, or Firm* — Merchant & Gould P.C.

(57) ABSTRACT

Novel intermediates, process for their preparation and their use in the preparation of therapeutically effective antineoplastic agents, in particular Temsirolimus of formula (I).

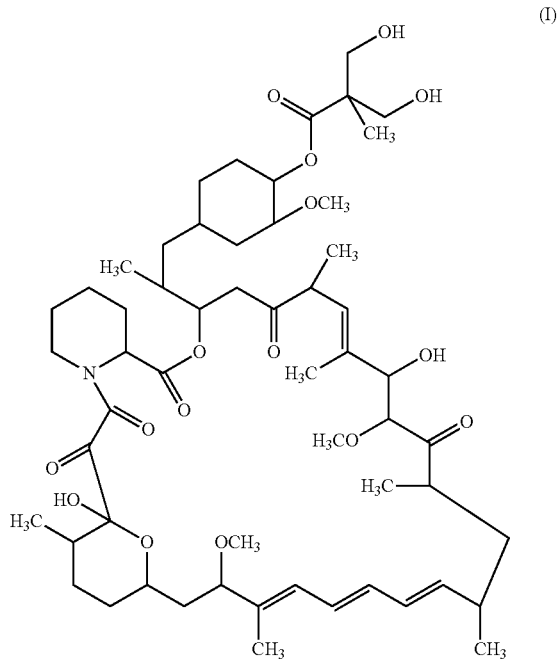

29 Claims, No Drawings

PROCESS FOR THE PREPARATION OF TEMSIROLIMUS AND ITS INTERMEDIATES

This application claims benefit of Serial No. 173/DEL/2010, filed 28 Jan. 2010 in India and which application is incorporated herein by reference. To the extent appropriate, a claim of priority is made to the above disclosed application.

FIELD OF THE INVENTION

The present invention relates to novel intermediates, process for their preparation and their use in the preparation of therapeutically effective antineoplastic agents, in particular Temsirolimus of formula (I).

BACKGROUND OF THE INVENTION

Temsirolimus (CCI-779), an mTOR kinase Inhibitor of formula (I) is an antineoplastic agent indicated for the treatment of advanced renal cell carcinoma. Temsirolimus is a Rapamycin 42 ester with [3-hydroxy-2-(hydroxymethyl)-2-methylpropanoic acid and was first disclosed by Skotnicki et al in U.S. Pat. No. 5,362,718.

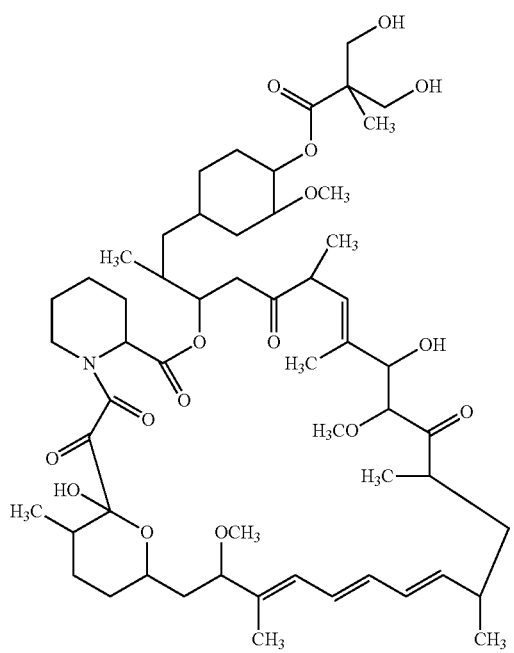

Several processes for the preparation of Temsirolimus have been reported in the literature such as those described in U.S. Pat. No. 5,362,718; U.S. Pat. No. 6,277,983 and U.S. Pat. No. 7,153,957.

U.S. Pat. No. 5,362,718 discloses a process for the preparation of different rapamycin 42 esters including Temsirolimus as per the scheme given below (Scheme-I).

Scheme-I: Synthesis of Temsirolimus as disclosed in U.S. Pat. No. 5,362,718

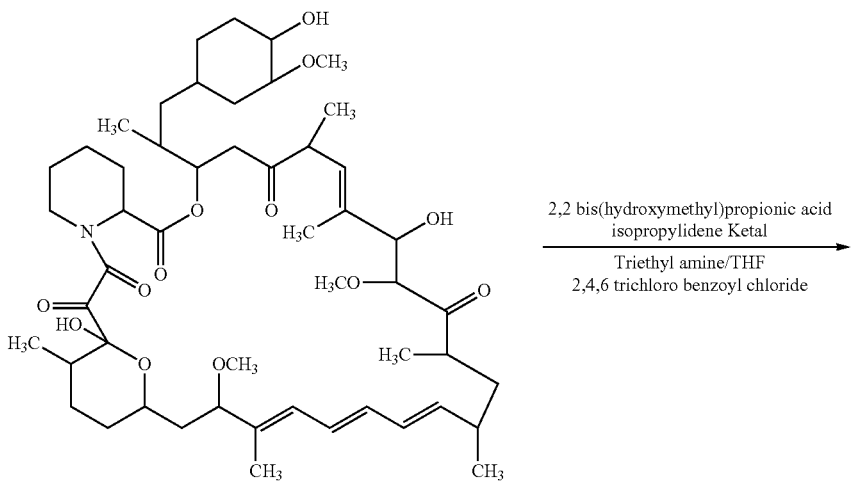

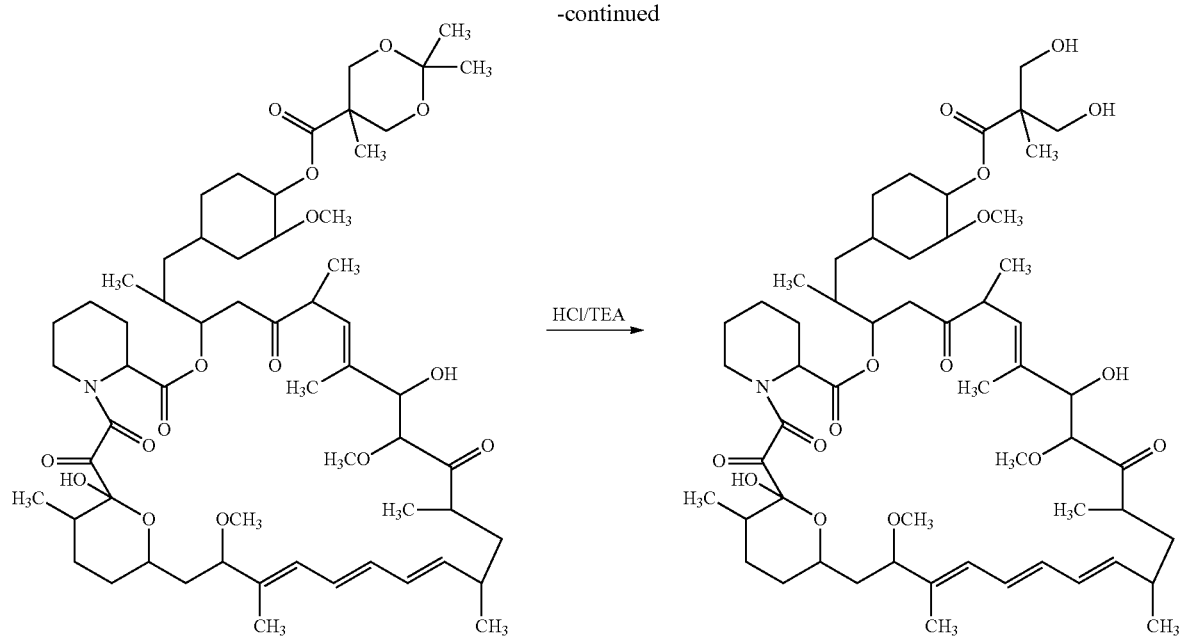

The process is non-regioselective and hence results in 31-esterified rapamycin, 31, 42 diesterified rapamycin and unreacted rapamycin along with the desired rapamycin-42 ester.

U.S. Pat. No. 6,277,983 reports a process for the preparation of Temsirolimus by using 31, 42 bis silyl intermediates as per the scheme shown below (Scheme-II).

Scheme-II:
Synthesis of Temsirolimus as disclosed in U.S. Pat. No. 6,277,983

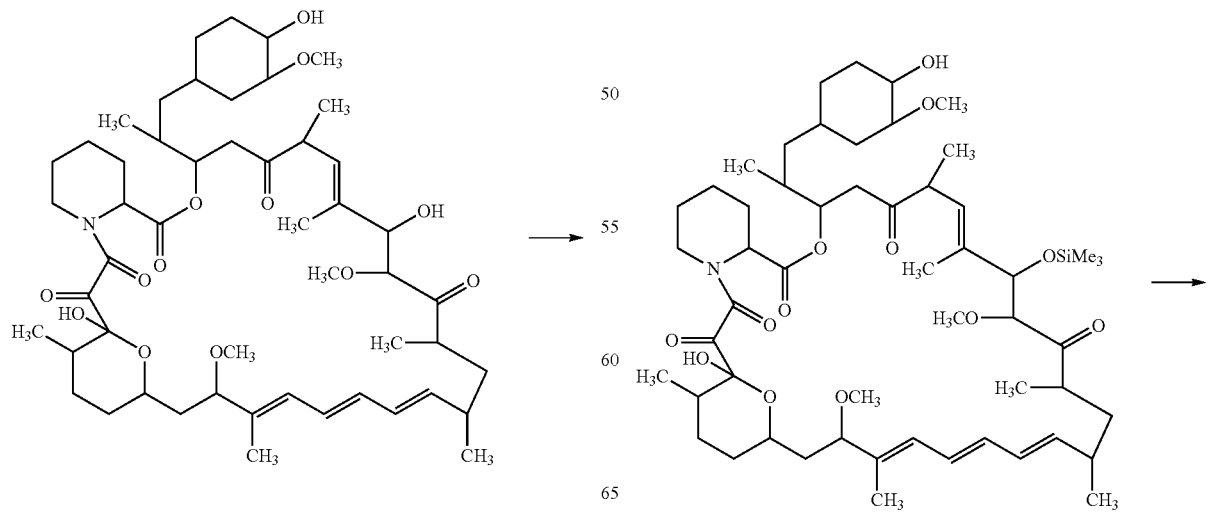

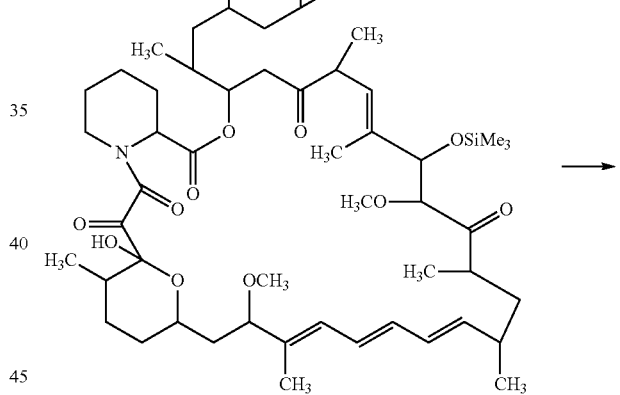

5
-continued
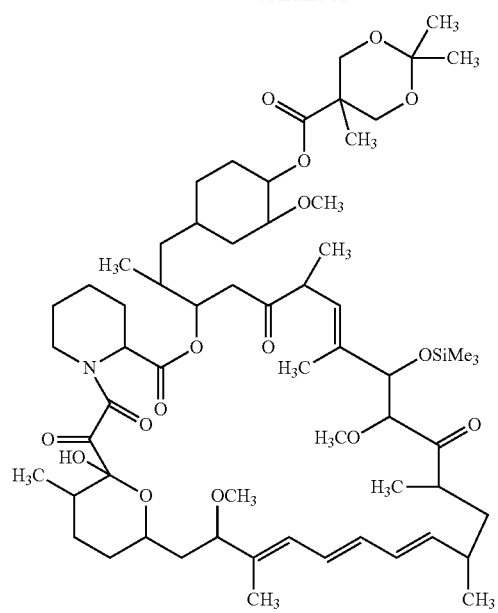
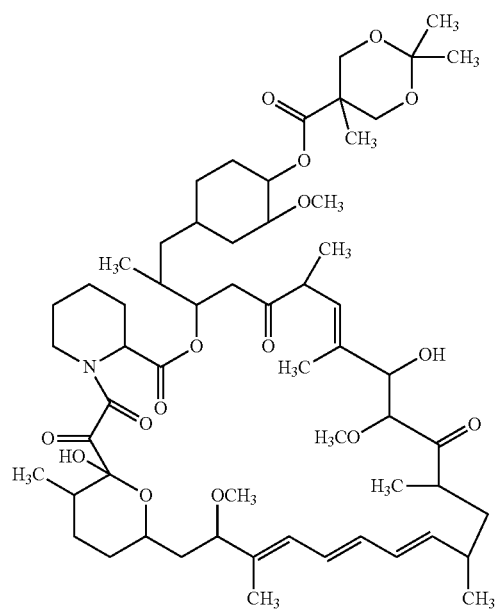
6
-continued
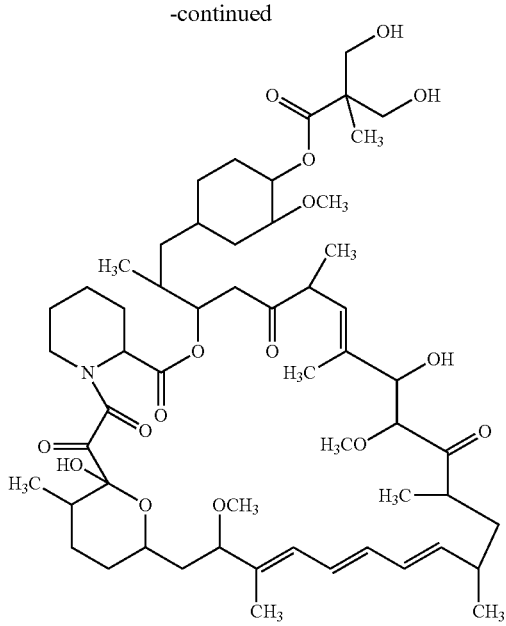
U.S. Pat. No. 7,153,957 reports a process for the preparation of Temsirolimus by using boronate intermediate as per the scheme shown below (Scheme-III).
Scheme-III:
Synthesis of Temsirolimus as disclosed in U.S. Pat. No. 7,153,957
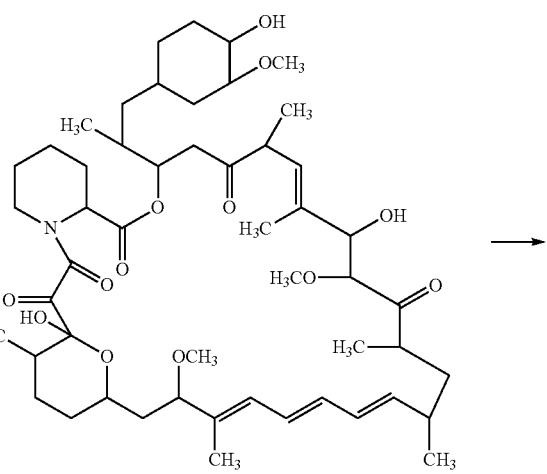

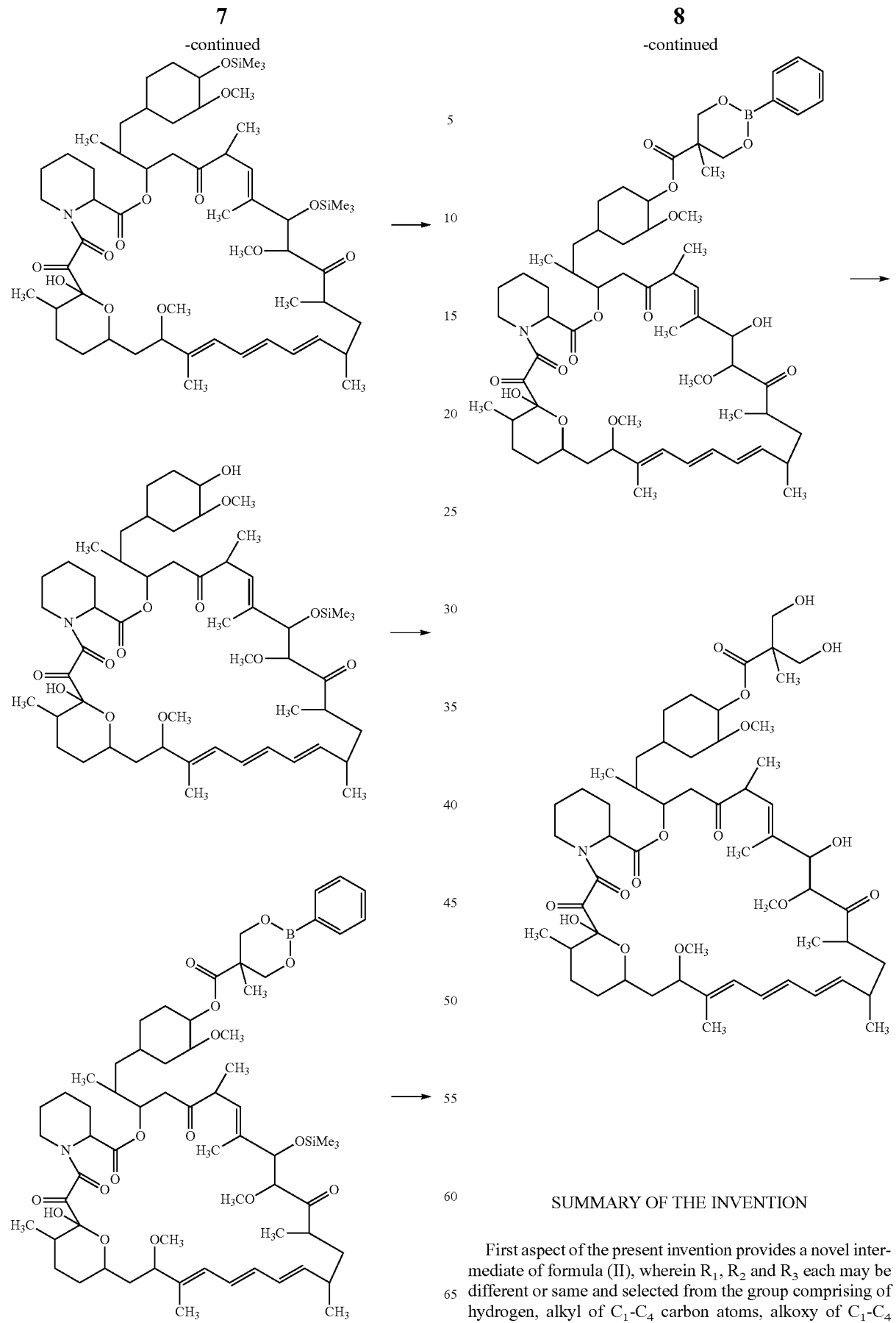
SUMMARY OF THE INVENTION
First aspect of the present invention provides a novel intermediate of formula (II), wherein $R_1$, $R_2$ and $R_3$ each may be different or same and selected from the group comprising of hydrogen, alkyl of $C_1$-$C_4$ carbon atoms, alkoxy of $C_1$-$C_4$ carbon atoms.

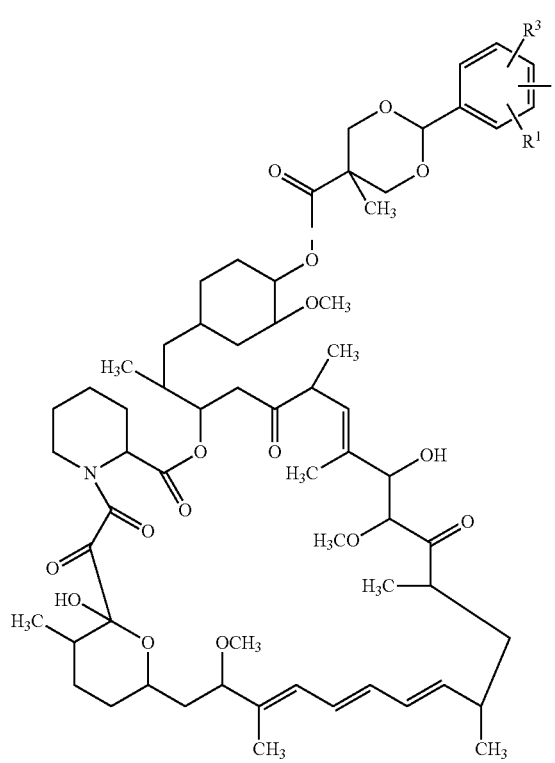

(II)

Second aspect of the present invention provides a novel intermediate of formula (II'), wherein each $R_1$ and $R_2$ is hydrogen and $R_3$ is methoxy.

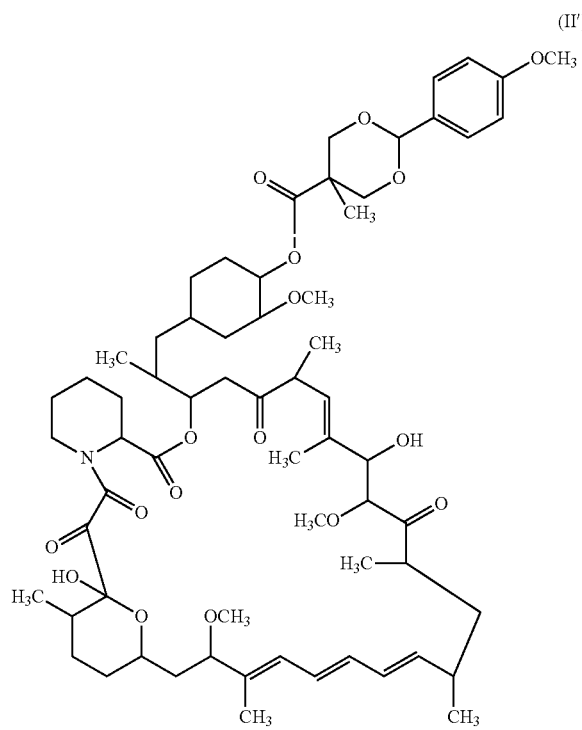

(II')

Third aspect of the present invention provides a novel intermediate of formula (II''), wherein $R_1$ is hydrogen, $R_2$ is methyl and $R_3$ is methoxy.

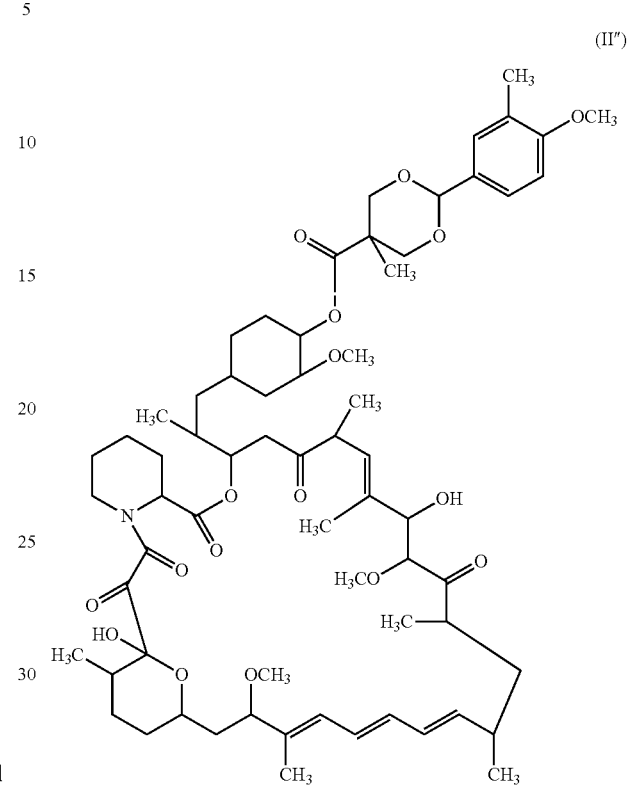

(II'')

Fourth aspect of the present invention provides a novel intermediate of formula (IV), wherein $R_1$, $R_2$ and $R_3$ each may be different or same and selected from the group comprising of hydrogen, alkyl of $C_1$-$C_4$ carbon atoms, alkoxy of $C_1$-$C_4$ carbon atoms.

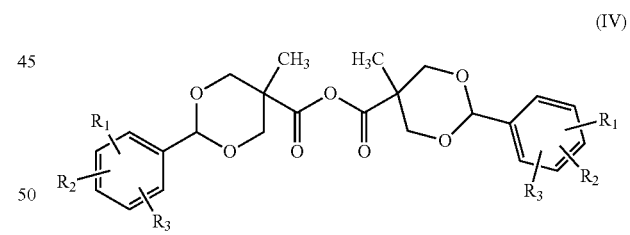

(IV)

Fifth aspect of the present invention provides a novel intermediate of formula (IV'), wherein each $R_1$ and $R_2$ is hydrogen and $R_3$ is methoxy.

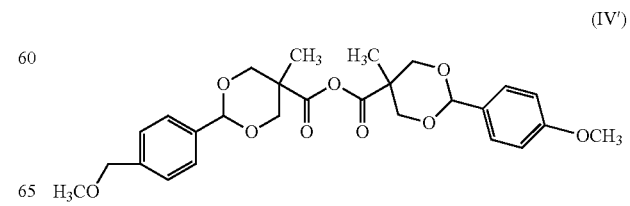

(IV')

Sixth aspect of the present invention provides a novel intermediate of formula (IV″), wherein $R_1$ is hydrogen, $R_2$ is methyl and $R_3$ is methoxy.

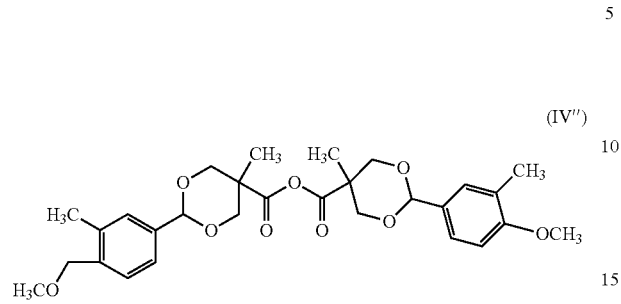

(IV″)

Seventh aspect of the present invention provides a process for the preparation of compound of formula (II) comprising treating rapamycin of formula (III) with a compound of formula (IV).

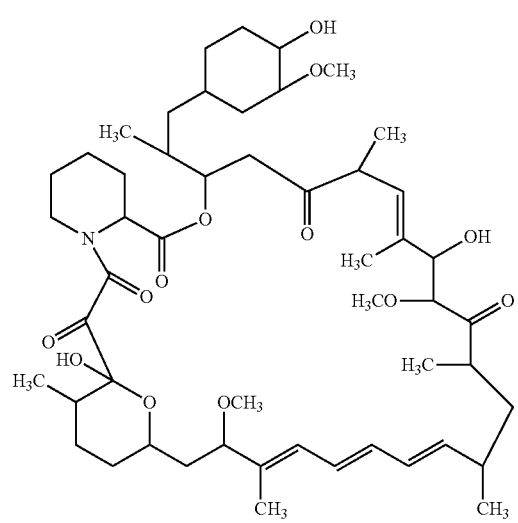

(III)

Eighth aspect of the present invention provides a process for the preparation of Temsirolimus comprising converting compound of formula (II) to Temsirolimus of formula (I).

Ninth aspect of the present invention provides a process for the preparation of compound of formula (IV) comprising the steps of:

a) treating compound of formula (V)

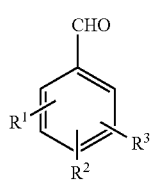

(V)

with trimethyl orthoformate to obtain the compound of formula (VI),

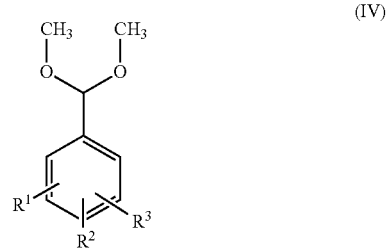

(IV)

b) treating compound of formula (VI) with 2,2-bis(hydroxymethyl)propionic acid to obtain the compound of formula (VII)

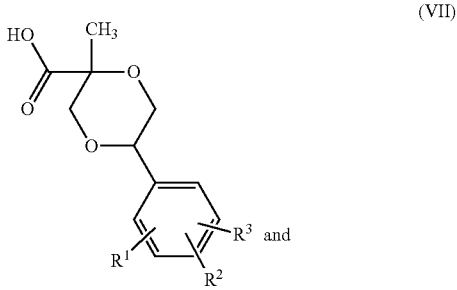

(VII)

c) treating compound of formula (VII) with a coupling agent to obtain the compound of formula (IV)

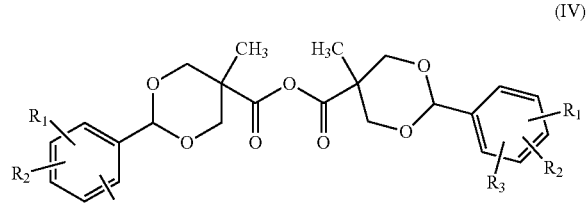

(IV)

DETAILED DESCRIPTION OF THE INVENTION

First aspect of the present invention provides a novel intermediate of formula (II), wherein $R_1$, $R_2$ and $R_3$ each may be different or same and selected from the group comprising of hydrogen, alkyl of $C_1$-$C_4$ carbon atoms, alkoxy of $C_1$-$C_4$ carbon atoms.

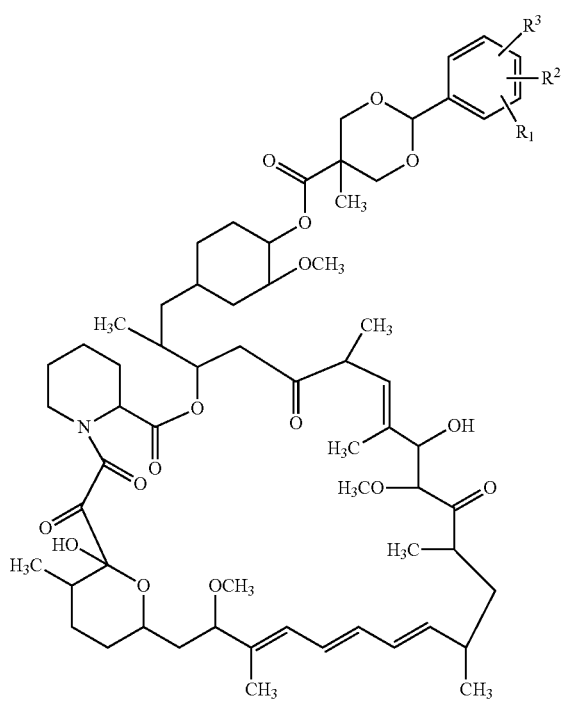

Second aspect of the present invention provides a novel intermediate of formula (II'), wherein each $R_1$ and $R_2$ is hydrogen and $R_3$ is methoxy.

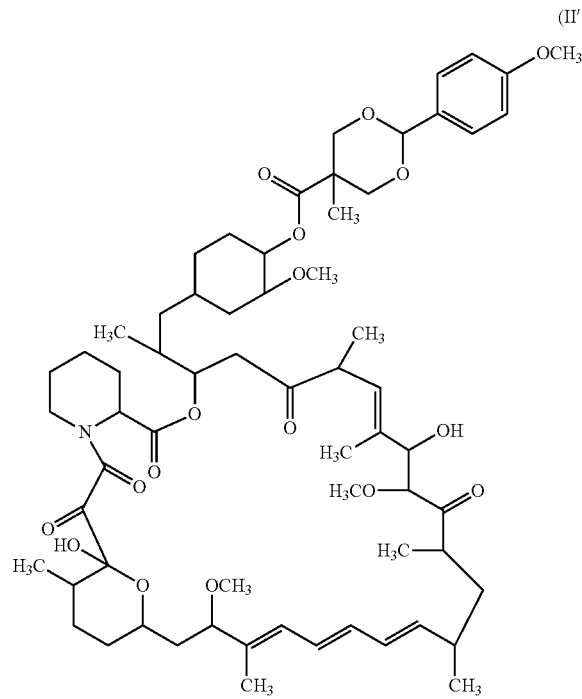 [SMILES: COc1ccc(C2OCC(C)(C(=O)OC3CCC(CC(C)C4CC(=O)C(C)/C=C(\C)C(O)C(OC)C(=O)C(C)CC(C)/C=C/C=C/C=C(\C)C(OC)CC5CCC(C)C(O)(O5)C(=O)C(=O)N5CCCCC5C(=O)O4)CC3OC)CO2)cc1]

Compound of formula (II') may be characterized by following NMR data:

$^{13}$C NMR (100 MHz, CDCl3) δ 17.74 & 19.20 (CH$_3$), 41.99 & 42.40 (C), 57.53 & 57.88 (OCH$_3$), 101.66 & 101.77 (CH), 113.51 & 113.68 (ArCH), 127.39 & 127.60 (ArCH), 173.56 & 177.47 (C=O; ester)

Compound of formula (II') may be further characterized by IR (KBr, cm$^{-1}$) spectrum having band at 1725 cm$^{-1}$.

Third aspect of the present invention provides a novel intermediate of formula (II''), wherein $R_1$ is hydrogen, $R_2$ is methyl and $R_3$ is methoxy.

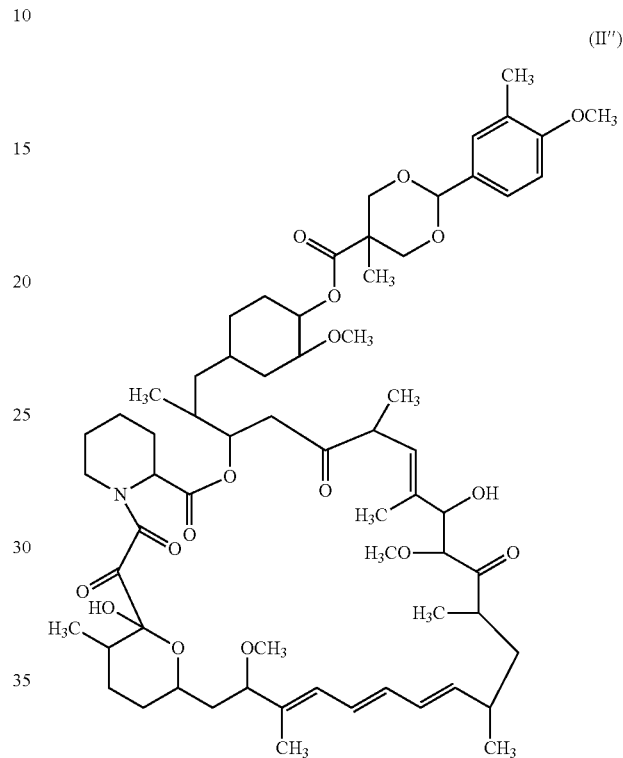

Compound of formula (II'') may be characterized by following NMR data:

$^1$HNMR (400 MHz, CDCl3) δ 3.31 (s, 3H), 3.35 (s, 3H), 3.78 (s, 3H), 2.07 (s, 3H), 1.24 (s, 3H), 4.16 (d, 1H), 6.74 (d, 8 Hz, 1H), 7.18 (5, 1H), 7.21 (d, 8 Hz, 2H), 7.24 (s, 1H), 5.94 (d, 10.4 Hz, 1H)

Fourth aspect of the present invention provides a novel intermediate of formula (IV), wherein $R_1$, $R_2$ and $R_3$ each may be different or same and selected from the group comprising of hydrogen, alkyl of $C_1$-$C_4$ carbon atoms, alkoxy of $C_1$-$C_4$ carbon atoms.

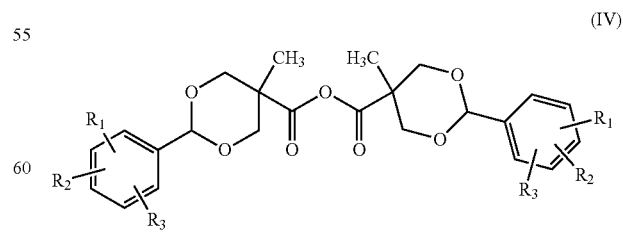

Fifth aspect of the present invention provides a novel intermediate of formula (IV'), wherein each $R_1$ and $R_2$ is hydrogen and $R_3$ is methoxy.

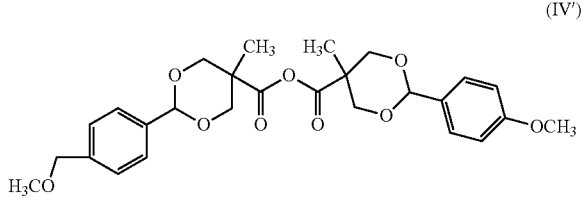 [SMILES: COCc1ccc(C2OCC(C)(C(=O)OC(=O)C3(C)COC(c4ccc(OC)cc4)OC3)CO2)cc1]

(IV')

Compound of formula (IV') may be characterized by following NMR data:

$^1$H NMR (400 MHz, CDCl3) δ δ 1.01 (s, 3H), 3.65 (d, J=11.2 Hz, 2H), 3.76 (s, 3H), 4.62 (d, J=11.2 Hz, 2H), 5.41 (s, 1H), 6.82 (d, J=8.8 Hz, 2H), 7.35 (d, J=8.8 Hz, 2H)

Compound of formula (II') may be further characterized by IR (KBr, cm$^{-1}$) spectrum having band at 1253, 1813 cm$^{-1}$ Sixth aspect of the present invention provides a novel intermediate of formula (IV''), wherein R$_1$ is hydrogen, R$_2$ is methyl and R$_3$ is methoxy.

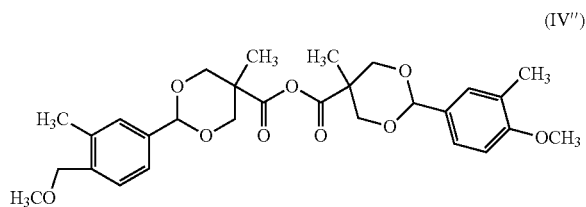 [SMILES: COCc1ccc(C2OCC(C)(C(=O)OC(=O)C3(C)COC(c4ccc(OC)c(C)c4)OC3)CO2)cc1C]

(IV'')

Compound of formula (IV'') may be characterized by following NMR data:

$^1$H NMR (400 MHz, CDCl3) δ 1.12 (s, 3H), δ 2.17 (s, 3H), 3.65 (d, 11.5 Hz, 2H), 3.79 (s, 3H), 4.63 (d, 11.48 Hz, 2H), 5.39 (s, 1H), 6.74 (d, 8.2 Hz, 2H)

Seventh aspect of the present invention provides a process for the preparation of compound of Formula II comprising treating rapamycin of formula (III) with a compound of formula (IV).

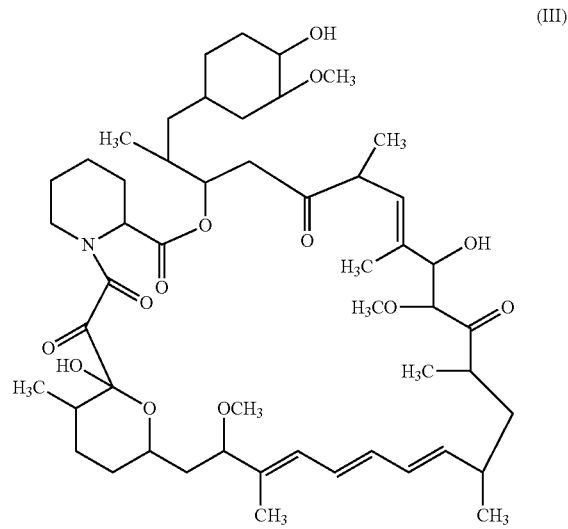 [SMILES: COC1CC2CCC(C)C(O)(O2)C(=O)C(=O)N2CCCCC2C(=O)OC(C(C)CC2CCC(O)C(OC)C2)CC(=O)C(C)/C=C(\C)C(O)C(OC)C(=O)C(C)CC(C)/C=C/C=C/C=C/1C]

(III)

The reaction of rapamycin with compound of formula (IV) may be carried out in the presence of suitable solvents. Suitable solvents may be selected from the group comprising of halogenated hydrocarbons such as ethylene chloride, methylene chloride, carbon tetra chloride and mixtures thereof.

The reaction of rapamycin with compound of formula (IV) may be carried out in the presence of catalytic amount of Dimethyl amino pyridine (DMAP) or 4-Pyrrolidinopyridine (PPY).

The reaction of rapamycin with compound of formula (IV) may be carried out at a temperature range of about −20° C. to about room temperature. Preferably the reaction may be carried out at the temperature range of 0° C. to about 5° C.

The reaction of rapamycin with compound of formula (IV) may be carried out for about 6-24 hours. Preferably the reaction may be carried out for about 18 hours.

Eighth aspect of the present invention provides a process for the preparation of Temsirolimus comprising converting compound of formula (II) to Temsirolimus of formula (I).

The conversion of compound of formula (II) to Temsirolimus may be carried out in the presence of an acid. An acid may be selected from the group comprising of sulfuric acid, hydrochloric acid and mixtures thereof.

The conversion of compound of formula (II) to Temsirolimus may be carried out in the presence of suitable solvents. Suitable solvent may be selected from the group comprising of alcohols such as methanol, ethanol, propanol, butanol and mixtures thereof; ethers such as tetrahydrofuran, dioxane or mixtures thereof.

The conversion of compound of formula (II) to Temsirolimus may be carried out at a temperature range of about −20° C. to about room temperature. Preferably the reaction may be carried out at the temperature range of 0° C. to about 5° C.

The conversion of compound of formula (II) to Temsirolimus may be carried out for about 6-24 hours. Preferably the reaction may be carried out for about 18 hours.

Temsirolimus may be further purified by known techniques like column chromatography and crystallization.

Ninth aspect of the present invention provides a process for the preparation of compound of formula (IV) comprising the steps of:

a) treating compound of formula (V)

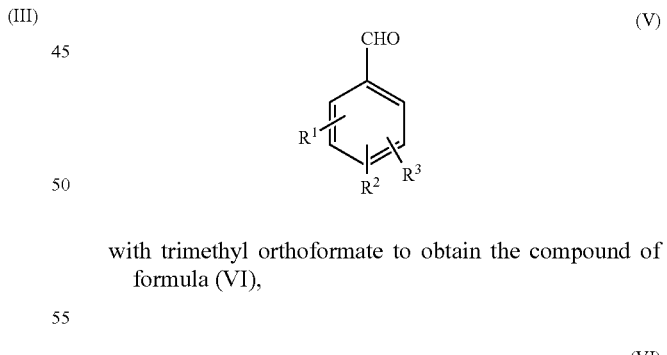

(V)

with trimethyl orthoformate to obtain the compound of formula (VI),

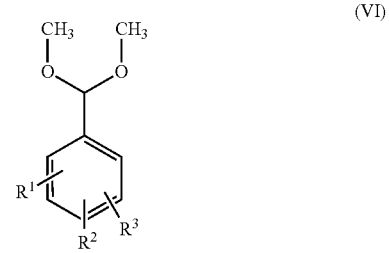

(VI)

b) treating compound of formula (VI) with 2,2-bis(hydroxymethyl)propionic acid to obtain the compound of formula (VII)

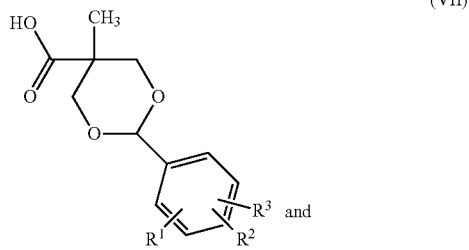

(VII)

and c) treating compound of formula (VII) with a coupling agent to obtain the compound of formula (IV)

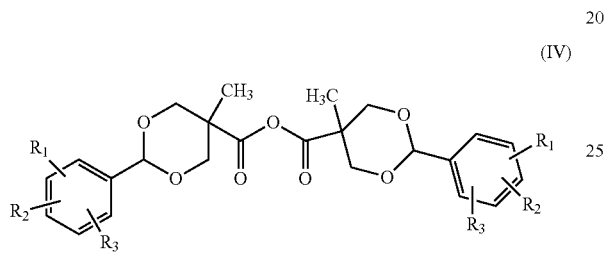

(IV)

The reaction of compound of formula (V) with trimethyl orthoformate may be carried out in the presence of suitable solvents. Suitable solvents may be selected from the group comprising of alcohols such as methanol, ethanol, propanol, butanol and mixtures thereof.

The reaction of compound of formula (V) with trimethyl orthoformate may be carried out in the presence of catalytic amount of an acid such as hydrochloric acid.

The reaction of compound of formula (V) with trimethyl orthoformate may be carried out at a temperature range of about 0° C. to about reflux temperature. Preferably the reaction may be carried out at room temperature.

The reaction of compound of formula (V) with trimethyl orthoformate may be carried out for about 6-24 hours. Preferably the reaction may be carried out for about 18 hours.

The reaction of compound of formula (VI) with 2,2-bis(hydroxymethyl)propionic acid may be carried out in the presence of suitable solvents. Suitable solvents may be selected from the group comprising of ketones such as acetone, methyl ethyl ketone, methyl isobutyl ketone and mixtures thereof;

The reaction of compound of formula (VI) with 2,2-bis(hydroxymethyl)propionic acid may be carried out in the presence of catalytic amount of an acid such as p-toluenesulfonic acid.

The reaction of compound of formula (VI) with 2,2-bis(hydroxymethyl)propionic acid may be carried out at a temperature range of about 0° C. to about reflux temperature. Preferably the reaction may be carried out at room temperature.

The reaction of compound of formula (VI) with 2,2-bis(hydroxymethyl)propionic acid may be carried out for about 2-10 hours. Preferably the reaction may be carried out for about 5-6 hours.

The reaction of compound of formula (VII) with coupling agent may be carried out in the presence of suitable solvent. Suitable solvent may be selected from the group comprising of ketones such as acetone, methyl ethyl ketone, methyl isobutyl ketone and mixtures thereof; halogenated hydrocarbons such as dichloromethane, dichloroethane and mixtures thereof.

Coupling agent may be selected from the group comprising of Dicyclohexylcarbodiimide (DCC) and 1-(3-Dimethylaminopropyl)-3-(ethylcarbodiimide) Hydrochloride (EDAC.HCl).

The reaction of compound of formula (VII) with coupling agent may be carried out at a temperature range of about 0° C. to about reflux temperature. Preferably the reaction may be carried out at room temperature.

The reaction of compound of formula (VII) with coupling agent may be carried out for about 6-24 hours. Preferably the reaction may be carried out for about 18 hours.

EXAMPLES

Example-1

Preparation of 1-(dimethoxymethyl)-4-methoxybenzene {anisaldehyde dimethyl acetal}

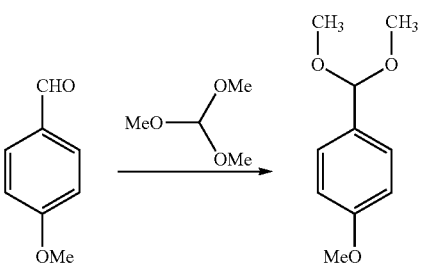

Anisaldehyde (40 g) and trimethylorthoformate (48.25 ml) were added to MeOH (60 ml) at 20-25° C. and the mixture was cooled to 10-15° C. Conc. HCl (0.26 ml) was then added to the mixture at 10-15° C. and was warmed to 20-25° C. followed by stirring at the same temperature for 16-18 hours. 5% aqueous KOH (40 ml) was added to the reaction mixture at 20-25° C. in 10 min and further stirred for 10 minutes. The reaction mixture was extracted with hexane (2×200 ml) and the combined organic layer was washed with DM water (200 ml). The organic layer was concentrated below 40° C. to obtain title compound (51.0 g, 95.2%).

Example-2

Preparation of 4-(dimethoxymethyl)-1-methoxy-2-methylbenzene {4-methoxy-3-methyl benzaldehyde dimethyl acetal}

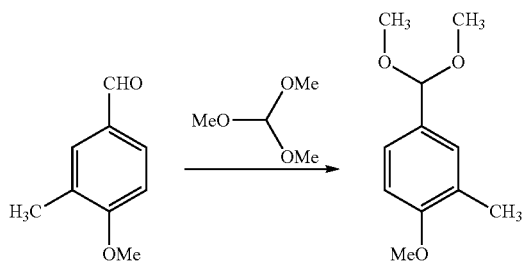

A solution of 4-methoxy-3-methyl benzaldehyde (10 g) and trimethylorthoformate (43.77 ml) in methanol (15 ml) was cooled to 5-10° C. Concentrated HCl (0.75 ml) was added and the reaction mixture was warmed to ambient temperature. The reaction mixture was stirred for 6 hours and quenched with 5% aqueous KOH (10 ml). The reaction mixture was extracted with hexane (100 ml) and the hexane layer was washed with water (100 ml). Hexane layer was dried over sodium sulfate and concentrated below 30° C. to obtain title compound (15.8 g).

MS(ES$^+$) (m/z) 219 [M+Na]$^+$

Example-3

Preparation of 2-(4-methoxyphenyl)-5-methyl-1,3-dioxane-5-carboxylic acid {2,2-bis(hydroxyl methyl) propionic acid anisylidene acetal

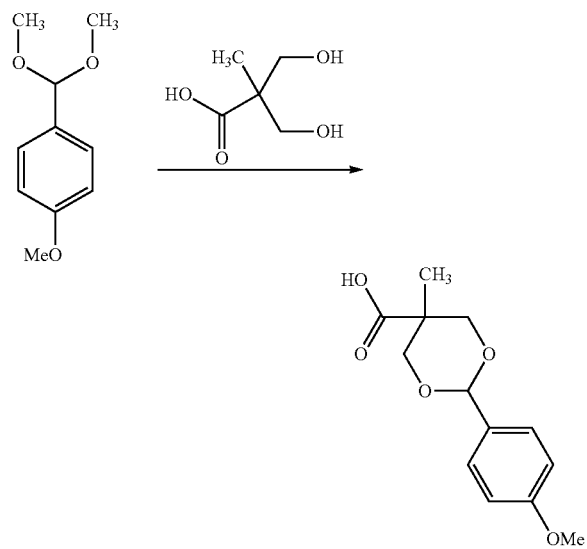

2,2-bis(hydroxymethyl)propionic acid (10 g) and anisaldehyde dimethyl acetal (20.4 g) were added to acetone (50 ml) at 20-25° C. p-Toluenesulfonic acid (0.51 g) was added to the reaction mixture and stirred at 20-25° C. for 5 hours. The mixture was then cooled to 0-5° C. and stirred for 1 hour. The slurry was filtered and the solid was washed with chilled (0-5° C.) acetone (10 ml). The solid was dried under vacuum at 45-50° C. for 4 hour. The solid was added to toluene (150 ml) and the resulting mixture was heated at 65-70° C. for 2 hours. The mixture was then cooled to 5-10° C. and stirred for 30 minutes. The slurry was filtered and the solid was washed with toluene (10 ml) followed by drying under vacuum at 30-35° C. for 4 hours to obtain title compound (14.0 g, 74.4%).

Example-4

Preparation of 2-(4-methoxy-3-methyl phenyl)-5-methyl-1,3-dioxane-5-carboxylic anhydride

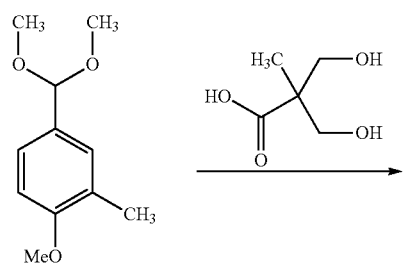

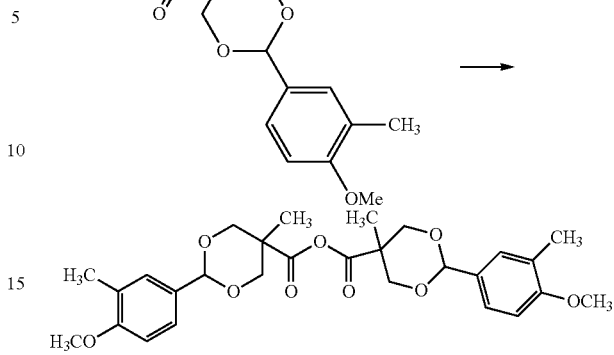

A mixture of 2,2-bis(hydroxymethyl)propionic acid (7.16 g), 4-methoxy-3-methyl benzaldehyde dimethyl acetal (15.0 g) and acetone (43 ml) was treated with p-toluenesulfonic acid (0.456 g) at ambient temperature and stirred for 7 h. The reaction mixture was cooled to 0-5° C. The slurry obtained was filtered and the solid was washed successively with acetone (43 ml) and dichloromethane (43 ml). A mixture of the wet solid and dichloromethane (43 ml) was treated with EDAC.HCl (4.4 g; 0.43 equivalents) at ambient temperature and stirred for 24 h. The reaction mixture was concentrated and the residue stirred with water (100 ml) for 30 min. The slurry was filtered and the solid dried under vacuum to obtain title compound (5.5 g).

$^1$H NMR (400 MHz, CDCl3) δ 1.12 (s, 3H), δ 2.17 (s, 3H), 3.65 (d, 11.5 Hz, 2H), 3.79 (s, 3H), 4.63 (d, 11.48 Hz, 2H), 5.39 (s, 1H), 6.74 (d, 8.2 Hz, 2H)

MS(ES$^+$) (m/z) 515 [M+H]$^+$, 532 [M+NH$_4$]$^+$, 537 [M+Na]$^+$

Example-5

Preparation of 2-(4-methoxyphenyl)-5-methyl-1,3-dioxane-5-carboxylic anhydride {2,2-bis(hydroxymethyl)propionic acid anisylidene acetal anhydride}

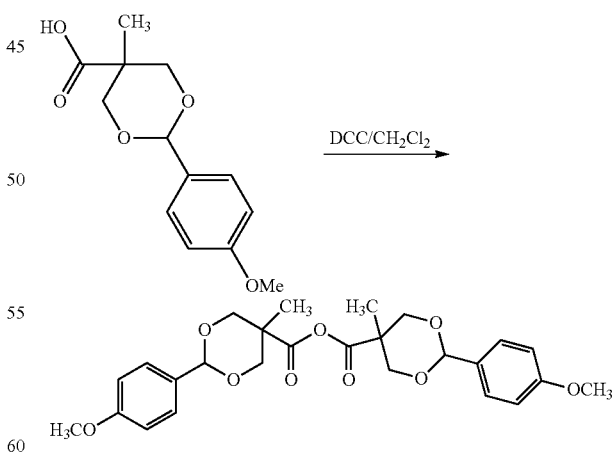

2,2-Bis(hydroxymethyl)propionic acid anisylidene acetal (10 g) and DCC (4.1 g) were added to CH$_2$Cl$_2$ (200 ml) at 20-25° C. and stirred for 18 hours. The mixture was heated to 30-35° C. and stirred for 1 hour. The slurry was filtered and the solid was washed with CH$_2$Cl$_2$ (20 ml). The filtrate was concentrated to dryness and toluene (150 ml) was added to residue at 20-25° C. The mixture was stirred at 20-25° C. for 1 hour and the slurry was filtered. The solid was washed with toluene (10 ml) and dried under vacuum at 30-35° C. for 4 hours to obtain title compound (7.5 g, 77.8%).

$^1$H NMR (400 MHz, CDCl3) δ δ 1.01 (s, 3H), 3.65 (d, J=11.2 Hz, 2H), 3.76 (s, 3H), 4.62 (d, J=11.2 Hz, 2H), 5.41 (s, 1H), 6.82 (d, J=8.8 Hz, 2H), 7.35 (d, J=8.8 Hz, 2H)

IR (KBr, cm$^{-1}$) 1253, 1813

M/z (ES$^+$) 487 [M+H]$^+$, 504 [M+NH$_4$]$^+$

Example-6

Preparation of Temsirolimus Acetal

Rapamycin (1.0 g) and anhydride (5.3 g) obtained in Example-5 were added to CH$_2$Cl$_2$ (10 ml) at 20-25° C. The mixture was then cooled to 0-5° C. and a solution of DMAP (1.5 g) in CH$_2$Cl$_2$ (5 ml) was added in 15 minutes. The reaction mixture was stirred at 0-5° C. for 18 hours. The reaction mixture was washed with DM water (10 ml). The organic layer was washed with 0.5N H$_2$SO$_4$ (15 ml), 5% aqueous NaHCO3 (20 ml) and DM water (10 ml). The organic layer was concentrated to dryness and the residue was purified by flash chromatography on silica gel using acetone-dichloromethane (2:23) as eluent to obtain title compound (0.6 g, 47.8%).

$^{13}$C NMR (100 MHz, CDCl3) δ 17.74 & 19.20 (CH$_3$), 41.99 & 42.40 (C), 57.53 & 57.88 (OCH$_3$), 101.66 &101.77

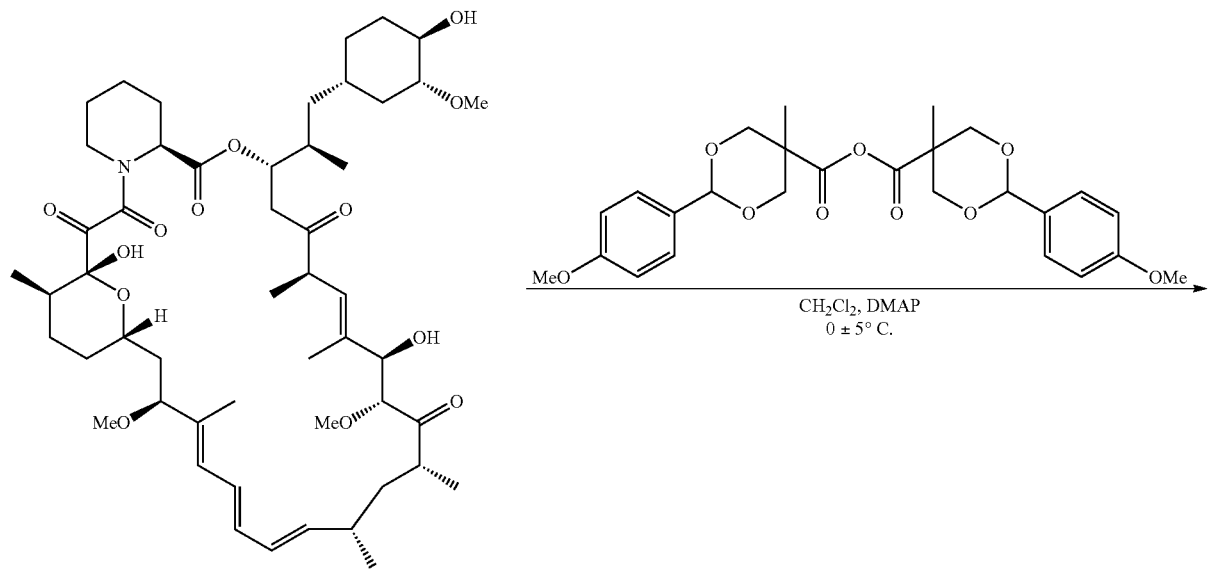

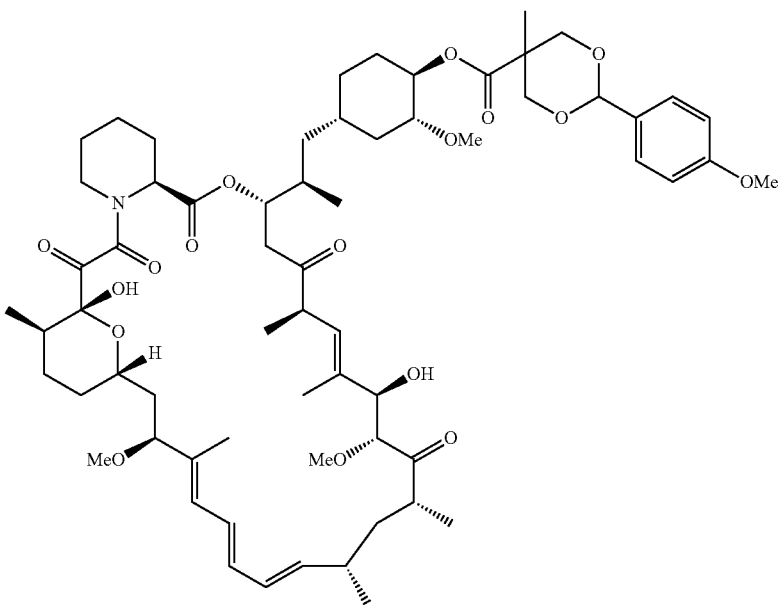

(CH), 113.51 & 113.68 (ArCH), 127.39 &127.60 (ArCH), 173.56 & 177.47 (C=O; ester)

IR (KBr, cm$^{-1}$) 1725
M/z (ES$^+$) 1166 [M+NH$_4$]$^{30}$
M/z (ES$^-$) 1147 [M−H]$^-$

Example-7

Preparation of Temsirolimus Methyl Acetal

A solution of rapamycin (0.5 g) and 2-(4-methoxy-3-methyl phenyl)-5-methyl-1,3-dioxane-5-carboxylic anhydride (0.702 g) obtained in Example-4 in dichloromethane (7.5 ml) was cooled to 0-5° C. and treated with a solution of 4-pyrrolidinopyridine (0.162 g) in dichloromethane (2.5 ml). The reaction mixture was stirred at 0-5° C. for 10 hours and quenched with water (10 ml). Organic layer was concentrated and the residue subjected to column chromatography over silica gel using acetone-dichloromethane (1:10) to obtain title compound (0.11 g).

$^1$HNMR (400 MHz, CDCl3) δ 3.31 (s, 3H), 3.35 (s, 3H), 3.78 (s, 3H), 2.07 (s, 3H), 1.24 (s, 3H), 4.16 (d, 1H), 6.74 (d, 8 Hz, 1H), 7.18 (5, 1H), 7.21 (d, 8 Hz, 2H), 7.24 (s, 1H), 5.94 (d, 10.4 Hz, 1H)

MS(ES$^+$) (m/z) 1180 [M+NH$_4$]$^+$, 1185 [M+Na]$^+$

Example-8

Preparation of Temsirolimus

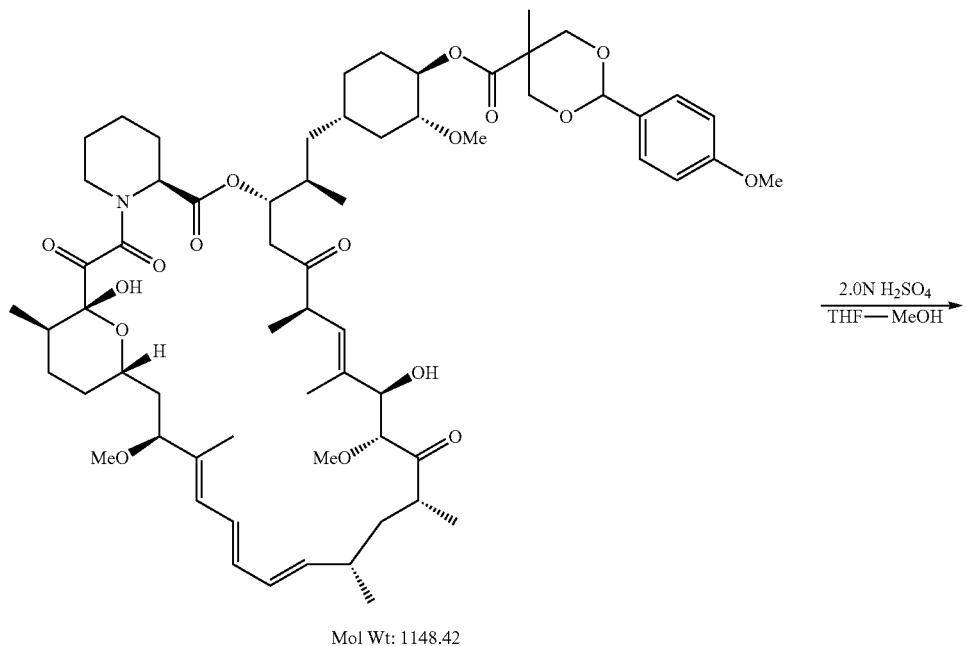

Mol Wt: 1148.42

2.0N H$_2$SO$_4$
———————→
THF—MeOH

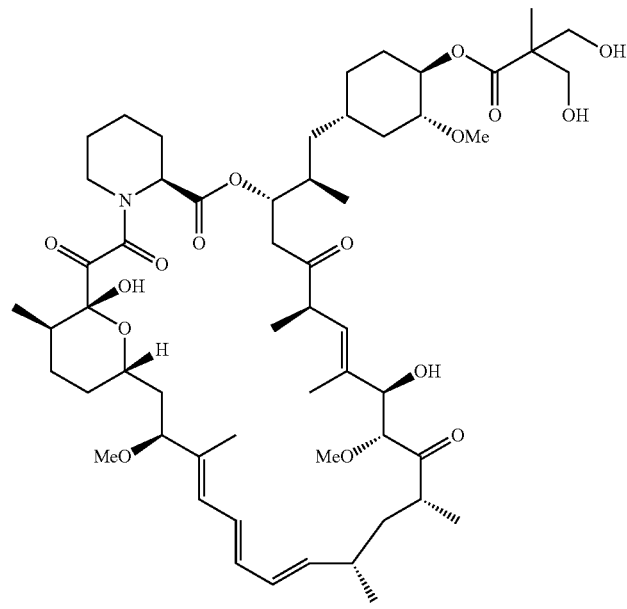

Mol Wt: 1030.29
TEMSIROLIMUS

Temsirolimus acetal (0.2 g) obtained in Example-6 was added to THF (3 ml) and MeOH (2 ml) at 20-25° C. The mixture was cooled to 0-5° C. and 2N aqueous $H_2SO_4$ (1 ml) was added to the mixture. The reaction mixture was stirred at 0-5° C. for 18 hours and extracted with EtOAc (10 ml). The organic layer was washed with 5% aqueous $NaHCO_3$ (10 ml) and DM water (10 ml). The organic layer was concentrated to dryness and the residue was purified by flash chromatography on silica gel using acetone-dichloromethane (1:4) as eluent to obtain title compound (0.1 g, 55.7%).

Example-9

Preparation of Temsirolimus

A mixture of Temsirolimus methyl acetal (50 mg) obtained in Example-7, methanol (0.2 ml) and THF (0.3 ml) was cooled to 0-5° C. A solution of Conc. HCl (0.01 ml) in water (0.15 ml) was added and stirred for 24 hours. Water (1 ml) was added and the mixture was extracted with ethyl acetate (3×2 ml). Combined organic layer was washed with 5% NaHCO3 (1 ml) and concentrated to dryness. The residue was purified by column chromatography over silica gel using acetone-hexane (1:3) to obtain title compound (30 mg).

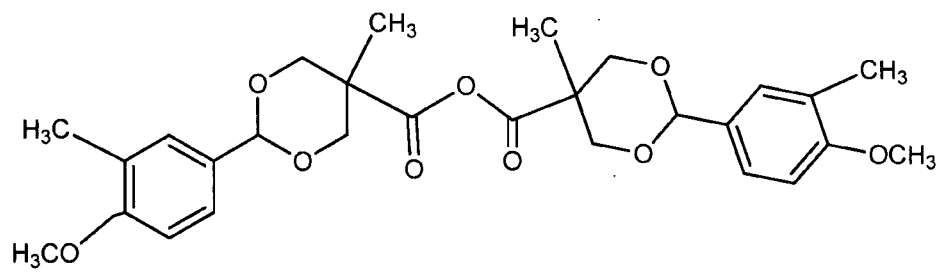

The invention claimed is:

1. A process for the preparation of Temsirolimus of formula (I),

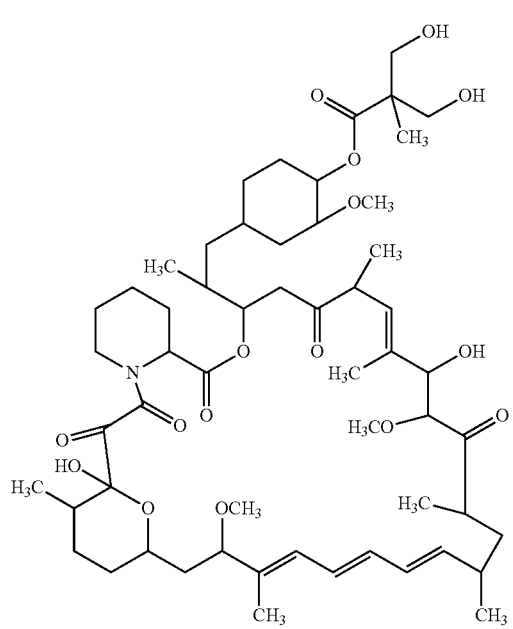

(I)

the method comprising converting compound of formula (II),

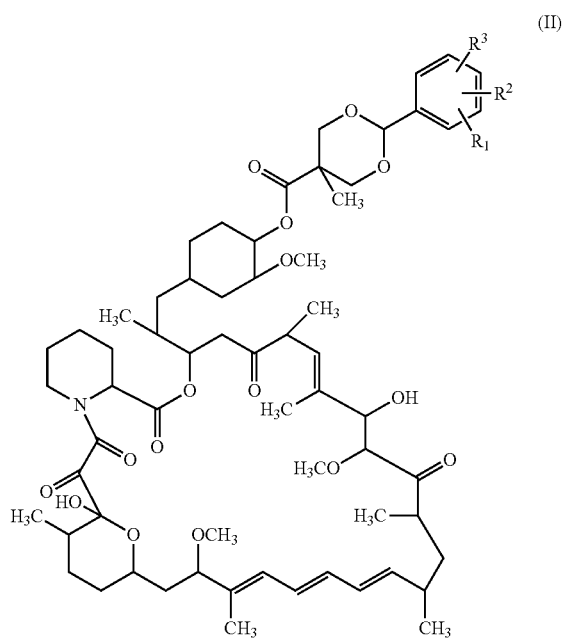

(II)

wherein $R_1$, $R_2$ and $R_3$ each may be different or same and selected from the group comprising hydrogen, alkyl of $C_1$-$C_4$ carbon atoms, and alkoxy of $C_1$-$C_4$ carbon atoms, to Temsirolimus;

in the presence of an acid, selected from the group comprising sulfuric acid, hydrochloric acid and mixtures thereof; and in the presence of a solvent selected from the group comprising alcohols and ethers or mixture thereof.

2. The process according to claim 1, wherein the solvent is selected from methanol, ethanol, propanol, butanol, and a mixture thereof.

3. The process according to claim 1, wherein the solvent is selected from tetrahydrofuran, dioxane, and a mixture thereof.

4. The process according to claim 1, wherein the conversion of compound of formula (II) to Temsirolimus is carried out at a temperature range of about −20° C. to about room temperature.

5. The process according to claim 1, wherein the conversion of compound of formula (II) to Temsirolimus is carried out for about 6-24 hours.

6. The process according to claim 1, wherein compound of Formula II is prepared by a process comprising treating rapamycin of formula (III),

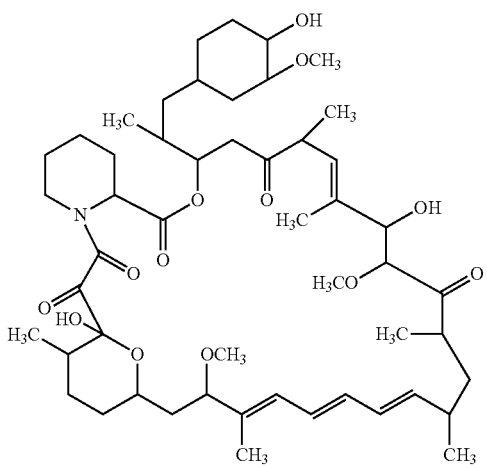

(III)

with a compound of formula (IV),

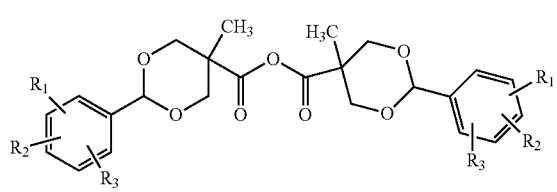

(IV)

wherein $R_1$, $R_2$ and $R_3$ each may be different or same and selected from the group comprising of hydrogen, alkyl of $C_1$-$C_4$ carbon atoms, alkoxy of $C_1$-$C_4$ carbon atoms.

7. The process according to claim 6, wherein the reaction of rapamycin with compound of formula (IV) is carried out in the presence of halogenated hydrocarbon.

8. The process according to claim 6, wherein the reaction of rapamycin with compound of formula (IV) is carried out in the presence of catalytic amount of Dimethyl amino pyridine or 4-Pyrrolidinopyridine.

9. The process according to claim 6, wherein the reaction of rapamycin with compound of formula (IV) is carried out at a temperature range of about −20° C. to about room temperature.

10. The process according to claim 6, wherein the reaction of rapamycin with compound of formula (IV) is carried out for about 6-24 hours.

11. The process according to claim 6, wherein compound of formula (IV) is prepared by a process comprising:

a) treating compound of formula (V)

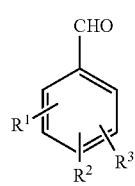

(V)

with trimethyl orthoformate to obtain the compound of formula (VI),

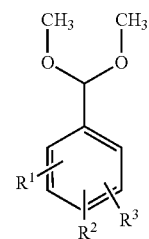

(VI)

b) treating compound of formula (VI) with 2,2-bis(hydroxymethyl)propionic acid to obtain the compound of formula (VII)

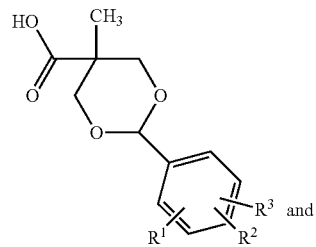

(VII) and c) treating compound of formula (VII) with a coupling agent to obtain the compound of formula (IV)

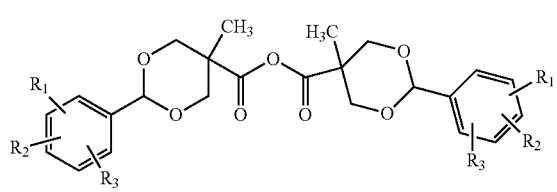

(IV)

wherein $R_1$, $R_2$ and $R_3$ each may be different or same and selected from the group comprising of hydrogen, alkyl of $C_1$-$C_4$ carbon atoms, alkoxy of $C_1$-$C_4$ carbon atoms.

12. The process according to claim 11, wherein the reaction of compound of formula (V) with trimethyl orthoformate is carried out in the presence of alcohol solvent.

13. The process according to claim 11, wherein the reaction of compound of formula (V) with trimethyl orthoformate is carried out in the presence of catalytic amount of an acid.

14. The process according to claim 11, wherein the reaction of compound of formula (V) with trimethyl orthoformate is carried out at a temperature range of about 0° C. to about reflux temperature.

15. The process according to claim 11, wherein the reaction of compound of formula (V) with trimethyl orthoformate is carried out for about 6-24 hours.

16. The process according to claim 11, wherein the reaction of compound of formula (VI) with 2,2-bis(hydroxymethyl) propionic acid is carried out in the presence of ketone solvents.

17. The process according to claim 11, wherein the reaction of compound of formula (VI) with 2,2-bis(hydroxymethyl) propionic acid is carried out in the presence of catalytic amount of an acid such as p-toluenesulfonic acid.

18. The process according to claim 11, wherein the reaction of compound of formula (VI) with 2,2-bis(hydroxymethyl) propionic acid is carried out at a temperature range of about 0° C. to about reflux temperature.

19. The process according to claim 11, wherein the reaction of compound of formula (VI) with 2,2-bis(hydroxymethyl) propionic acid is carried out for about 2-10 hours.

20. The process according to claim 11, wherein the reaction of compound of formula (VII) with coupling agent is carried out in the presence of suitable solvent selected from the group comprising of ketones and halogenated hydrocarbons.

21. The process according to claim 11, wherein coupling agent is selected from the group comprising of Dicyclohexylcarbodiimide (DCC) and 1-(3-Dimethylaminopropyl)-3-(ethylcarbodiimide)Hydrochloride (EDAC.HCl).

22. The process according to claim 11, wherein the reaction of compound of formula (VII) with coupling agent is carried out at a temperature range of about 0° C. to about reflux temperature.

23. The process according to claim 11, wherein the reaction of compound of formula (VII) with coupling agent is carried out for about 6-24 hours.

24. The process according to claim 7, wherein the solvent is selected from ethylene chloride, methylene chloride, carbon tetrachloride, or a mixture thereof.

25. The process according to claim 12, wherein the solvent is selected from methanol, ethanol, propanol, butanol, or a mixture thereof.

26. The process according to claim 16, wherein the solvent is selected from acetone, methyl ethyl ketone, methyl isobutyl ketone, or a mixture thereof.

27. The process according to claim 20, wherein the solvent is selected from acetone, methyl ethyl ketone, methyl isobutyl ketone, or a mixture thereof.

28. The process according to claim 20, wherein the solvent is selected from dichloromethane, dichloroethane, or a mixture thereof.

29. The process of claim 13, wherein the acid is hydrochloric acid.

* * * * *

UNITED STATES PATENT AND TRADEMARK OFFICE
CERTIFICATE OF CORRECTION

PATENT NO.      : 8,524,893 B2
APPLICATION NO. : 13/016235
DATED           : September 3, 2013
INVENTOR(S)     : Nitin Gupta et al.

Page 1 of 2

It is certified that error appears in the above-identified patent and that said Letters Patent is hereby corrected as shown below:

In the Specification:

Col. 10, lines 60-65: structure (IV') should appear as:

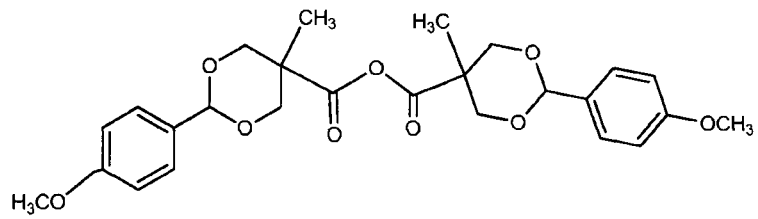

Col. 11, lines 10-15: structure (IV") should appear as:

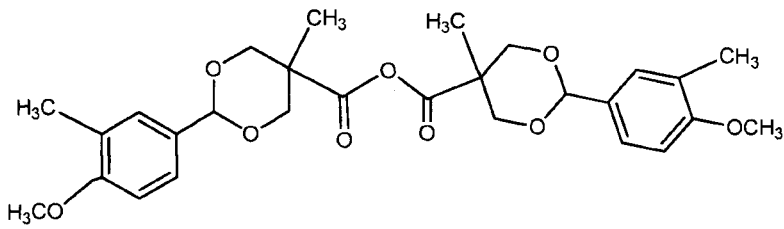

Col. 15, lines 3-8: structure (IV') should appear as:

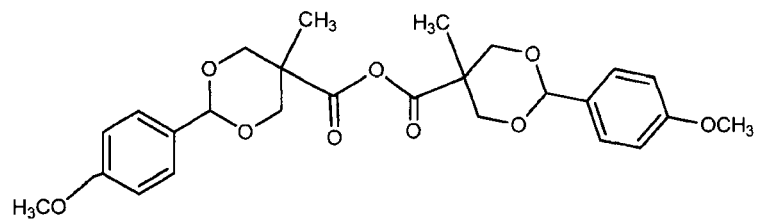

Signed and Sealed this
Twenty-ninth Day of April, 2014

Michelle K. Lee
*Deputy Director of the United States Patent and Trademark Office*

CERTIFICATE OF CORRECTION (continued)
U.S. Pat. No. 8,524,893 B2

Col. 15, lines 25-30: structure (IV'') should appear as: